(12) United States Patent
Willard

(10) Patent No.: US 10,856,936 B2
(45) Date of Patent: Dec. 8, 2020

(54) ELECTRODE ASSEMBLY FOR CATHETER SYSTEM INCLUDING THERMOPLASTIC-BASED STRUTS

(71) Applicant: St. Jude Medical, Cardiology Division, Inc., St. Paul, MN (US)

(72) Inventor: Steven Nicholas Willard, Bloomington, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 962 days.

(21) Appl. No.: 14/499,842

(22) Filed: Sep. 29, 2014

(65) Prior Publication Data

US 2015/0112327 A1 Apr. 23, 2015

Related U.S. Application Data

(60) Provisional application No. 61/894,667, filed on Oct. 23, 2013.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00136* (2013.01);
(Continued)

(58) Field of Classification Search
CPC ...... A61B 18/1492; A61B 2018/00136; A61B 2018/0016; A61B 2018/00267;
(Continued)

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

(Continued)

*Primary Examiner* — Daniel W Fowler
*Assistant Examiner* — Tigist S Demie
(74) *Attorney, Agent, or Firm* — Armstrong Teasdale LLP

(57) ABSTRACT

The present disclosure provides ablation catheter systems and electrode assemblies or baskets for use in the ablation catheter systems that include struts that are manufactured from a thermoplastic material. In many embodiments, the struts manufactured from a single piece of thermoplastic material. The struts are generally configured to operate in a double diamond formation, although an electrode basket including the struts described herein may include two, three, four or more diamonds, which may be of the same or different sizes. By manufacturing the struts from a thermoplastic material the diamond-shaped struts as described in the present disclosure may be manufactured with sufficient strength without the need for a nitinol frame or adhesives, thus reducing the overall cost of the strut, as well as overall manufacturing time.

16 Claims, 7 Drawing Sheets

(52) U.S. Cl.
CPC ............... *A61B 2018/00267* (2013.01); *A61B 2018/00357* (2013.01); *A61B 2018/00577* (2013.01); *A61B 2018/00821* (2013.01); *A61B 2018/00839* (2013.01)

(58) Field of Classification Search
CPC ........... A61B 2018/00357; A61B 2018/00577; A61B 2018/00821; A61B 2018/00839
See application file for complete search history.

(56) References Cited

U.S. PATENT DOCUMENTS

| | | | |
|---|---|---|---|
| 5,035,694 A | | 7/1991 | Kasprzyk et al. |
| 5,255,679 A | | 10/1993 | Imran |
| 5,300,068 A | | 4/1994 | Rosar et al. |
| 5,345,936 A | * | 9/1994 | Pomeranz ............ A61B 5/0422 600/374 |
| 5,368,591 A | | 11/1994 | Lennox et al. |
| 5,387,233 A | | 2/1995 | Alferness et al. |
| 5,465,717 A | | 11/1995 | Imran et al. |
| 5,531,779 A | | 7/1996 | Dahl et al. |
| 5,598,848 A | | 2/1997 | Swanson et al. |
| 5,607,462 A | | 3/1997 | Imran |
| 5,628,313 A | | 5/1997 | Webster, Jr. |
| 5,676,662 A | | 10/1997 | Fleischhacker et al. |
| 5,707,400 A | | 1/1998 | Terry, Jr. et al. |
| 5,769,077 A | | 6/1998 | Lindegren |
| 5,772,590 A | | 6/1998 | Webster, Jr. |
| 5,893,885 A | | 4/1999 | Webster, Jr. |
| 5,897,553 A | | 4/1999 | Mulier et al. |
| 5,954,649 A | | 9/1999 | Chia et al. |
| 5,954,719 A | | 9/1999 | Chen et al. |
| 6,004,269 A | | 12/1999 | Crowley et al. |
| 6,012,457 A | | 1/2000 | Lesh |
| 6,016,437 A | | 1/2000 | Tu et al. |
| 6,024,740 A | | 2/2000 | Lesh et al. |
| 6,073,048 A | | 6/2000 | Kieval et al. |
| 6,096,037 A | | 8/2000 | Mulier et al. |
| 6,117,101 A | | 9/2000 | Diederich et al. |
| 6,161,543 A | | 12/2000 | Cox et al. |
| 6,178,349 B1 | | 1/2001 | Kieval |
| 6,200,312 B1 | | 3/2001 | Zikorus et al. |
| 6,216,044 B1 | | 4/2001 | Kordis |
| 6,233,491 B1 | | 5/2001 | Kordis et al. |
| 6,283,951 B1 | | 9/2001 | Flaherty et al. |
| 6,287,608 B1 | | 9/2001 | Levin et al. |
| 6,292,695 B1 | | 9/2001 | Webster, Jr. et al. |
| 6,322,559 B1 | | 11/2001 | Daulton et al. |
| 6,425,895 B1 | * | 7/2002 | Swanson ............ A61B 18/1482 606/41 |
| 6,460,545 B2 | | 10/2002 | Kordis |
| 6,522,926 B1 | | 2/2003 | Kieval et al. |
| 6,613,045 B1 | | 9/2003 | Laufer et al. |
| 6,616,624 B1 | | 9/2003 | Kieval |
| 6,635,054 B2 | | 10/2003 | Fjield et al. |
| 6,656,174 B1 | | 12/2003 | Hedge et al. |
| 6,669,655 B1 | | 12/2003 | Acker et al. |
| 6,699,231 B1 | | 3/2004 | Sterman et al. |
| 6,748,255 B2 | | 6/2004 | Fuimaono et al. |
| 6,805,131 B2 | | 10/2004 | Kordis |
| 6,845,267 B2 | | 1/2005 | Harrison et al. |
| 6,954,977 B2 | | 10/2005 | Maguire et al. |
| 6,970,730 B2 | | 11/2005 | Fuimaono et al. |
| 7,122,031 B2 | | 10/2006 | Edwards et al. |
| 7,149,574 B2 | | 12/2006 | Yun et al. |
| 7,155,284 B1 | | 12/2006 | Whitehurst et al. |
| 7,162,303 B2 | | 1/2007 | Levin et al. |
| 7,245,955 B2 | | 7/2007 | Rashidi |
| 7,250,049 B2 | * | 7/2007 | Roop ................ A61B 18/1492 606/41 |
| 7,291,146 B2 | | 11/2007 | Steinke et al. |
| 7,363,076 B2 | | 4/2008 | Yun et al. |
| 7,419,486 B2 | | 9/2008 | Kampa |
| 7,465,288 B2 | | 12/2008 | Dudney et al. |
| 7,468,062 B2 | | 12/2008 | Oral et al. |
| 7,481,803 B2 | | 1/2009 | Kesten et al. |
| 7,653,438 B2 | | 1/2010 | Deem et al. |
| 7,717,948 B2 | | 5/2010 | Demarais et al. |
| 7,742,795 B2 | | 6/2010 | Stone et al. |
| 7,850,685 B2 | | 12/2010 | Kunis et al. |
| 7,949,407 B2 | | 5/2011 | Kaplan et al. |
| 8,145,316 B2 | | 3/2012 | Deem et al. |
| 8,224,416 B2 | | 7/2012 | de la Rama et al. |
| 8,343,213 B2 | | 1/2013 | Salahieh et al. |
| 8,347,891 B2 | | 1/2013 | Demarais et al. |
| 8,442,639 B2 | | 5/2013 | Walker et al. |
| 8,454,594 B2 | | 6/2013 | Demarais et al. |
| 8,545,495 B2 | | 10/2013 | Scheib |
| 9,022,948 B2 | | 5/2015 | Wang |
| 2002/0068885 A1 | | 6/2002 | Harhen et al. |
| 2002/0087208 A1 | * | 7/2002 | Koblish ............ A61B 18/1492 607/113 |
| 2002/0120304 A1 | | 8/2002 | Mest |
| 2003/0050681 A1 | | 3/2003 | Pianca et al. |
| 2003/0060858 A1 | | 3/2003 | Kieval et al. |
| 2003/0074039 A1 | | 4/2003 | Puskas |
| 2003/0114739 A1 | | 6/2003 | Fuimaono et al. |
| 2003/0216792 A1 | | 11/2003 | Levin et al. |
| 2003/0233099 A1 | | 12/2003 | Danaek et al. |
| 2004/0215186 A1 | | 10/2004 | Cornelius et al. |
| 2005/0288730 A1 | | 12/2005 | Deem |
| 2006/0089678 A1 | | 4/2006 | Shalev |
| 2007/0083193 A1 | * | 4/2007 | Werneth ............ A61B 5/0422 606/41 |
| 2007/0135875 A1 | | 6/2007 | Demarais et al. |
| 2008/0255478 A1 | | 10/2008 | Burdette |
| 2008/0262489 A1 | * | 10/2008 | Steinke ............ A61B 18/1492 606/33 |
| 2009/0076409 A1 | | 3/2009 | Wu et al. |
| 2010/0016762 A1 | | 1/2010 | Thapliyal et al. |
| 2010/0094209 A1 | | 4/2010 | Drasler et al. |
| 2010/0168737 A1 | | 7/2010 | Grunewald |
| 2010/0249773 A1 | | 9/2010 | Clark et al. |
| 2010/0268307 A1 | | 10/2010 | Demarais et al. |
| 2010/0286684 A1 | | 11/2010 | Hata et al. |
| 2011/0004087 A1 | | 1/2011 | Fish et al. |
| 2011/0118726 A1 | * | 5/2011 | De La Rama ..... A61B 18/1492 606/33 |
| 2011/0137298 A1 | | 6/2011 | Nguyen et al. |
| 2011/0160720 A1 | | 6/2011 | Johnson |
| 2011/0213231 A1 | | 9/2011 | Hall et al. |
| 2011/0257641 A1 | | 10/2011 | Hastings et al. |
| 2011/0264011 A1 | | 10/2011 | Wu et al. |
| 2011/0264086 A1 | | 10/2011 | Ingle |
| 2012/0143097 A1 | | 6/2012 | Pike, Jr. |
| 2012/0143181 A1 | * | 6/2012 | Demarais ................ A61N 1/32 606/41 |
| 2012/0143298 A1 | | 6/2012 | Just et al. |
| 2012/0271135 A1 | * | 10/2012 | Burke ................ A61B 5/0422 600/373 |
| 2012/0296232 A1 | | 11/2012 | Ng |
| 2012/0323233 A1 | | 12/2012 | Maguire et al. |
| 2013/0116737 A1 | | 5/2013 | Edwards et al. |
| 2013/0131743 A1 | | 5/2013 | Yamasaki et al. |
| 2013/0144251 A1 | | 6/2013 | Sobotka |
| 2013/0172715 A1 | | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |

(56) References Cited

FOREIGN PATENT DOCUMENTS

| WO | 2012/064818 | 5/2012 |
|----|-------------|--------|
| WO | 2012/106492 | 8/2012 |

OTHER PUBLICATIONS

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19-26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, Vol. 41, No. 2. February 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

(56) References Cited

OTHER PUBLICATIONS

Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65,729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-513.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.

(56) References Cited

OTHER PUBLICATIONS

Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3):139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Zazgornik, Jan et al, Bilateral Nephrectomy: The Best, but Often Overlooked, Treatment for Refractory Hypertension in Hemodialysis Patients, AJH 1998; 11:1364-1370.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.

(56) References Cited

OTHER PUBLICATIONS

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of the American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, K. Shoei Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Abboud, Francois M., The Sympathetic System in Hypertension, State-of-the-Art Review, Hypertension Journal of the American Heart Association, Hypertension 4 (suppl II):II-208-I-225, 1982.

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

Brookes, Linda et al, Renal Denervation: Is Reality Meeting Expectations?, An Interview with Michel Azizi, MD, PhD, Medscape, Jan. 7, 2013.

Bunte, Matthew C. et al, Endovascular Treatment of Resistant and Uncontrolled Hypertension, JACC: Cardiovascular Interventions, vol. 6, No. 1, 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

Campese, V.M., Is Hypertension in Chronic Renal Failure Neurogenic in Nature?, Nephrol Dial Transplant, 1994, 9: 741-742.

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of

(56) References Cited

OTHER PUBLICATIONS

Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Robbins, Ivan M. et al, Pulmonary Vein Stenosis After Catheter Ablation of Atrial Fibrillation, Circulation Journal of the American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of The American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.

(56) References Cited

OTHER PUBLICATIONS

Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.

* cited by examiner

ELECTRODE ASSEMBLY FOR CATHETER SYSTEM INCLUDING THERMOPLASTIC-BASED STRUTS

CROSS-REFERENCE TO RELATED APPLICATIONS

This application claims priority to provisional application Ser. No. 61/894,667, filed Oct. 23, 2013, the entire specification of which is incorporated herein.

FIELD OF THE DISCLOSURE

The present disclosure relates generally to a catheter system for use in a human body, and more particularly to catheter system including an electrode assembly having one or more struts fabricated from a thermoplastic material.

BACKGROUND ART

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient. The catheter typically carries one or more working components, such as electrodes and thermocouples, or other diagnostic, therapeutic or ablative devices for carrying out the procedures. One or more controls or actuators may be provided on the handle for selectively adjusting one or more characteristics of the working components.

One particular example of a multi-electrode catheter system is an ablative catheter system in which the working component is a multi-electrode assembly carried at the distal end of a flexible catheter. A control wire generally extends within the catheter from the multi-electrode assembly to the handle to operatively connect the multi-electrode assembly to an actuator on the handle. Manipulating the actuator acts on the control wire to configure the multi-electrode assembly into a desired configuration for carrying out the ablative procedure. For example, in one such ablative catheter system made by St. Jude Medical, Inc. under the trade name EnligHTN, the multi-electrode assembly is an electrode assembly in the general form of an electrode basket. The electrode basket generally includes a number of nitinol struts, wherein each strut may include one or two electrodes. The electrode basket is formed using the nitinol struts in combination with an adhesive material that is used at certain points to hold the electrode basket together for use in an ablation procedure.

BRIEF SUMMARY OF THE DISCLOSURE

In one embodiment, the present disclosure is directed to an electrode assembly for an ablation catheter system. The electrode assembly comprises at least one strut constructed from a thermoplastic material and includes at least one electrode.

In another embodiment, the present disclosure is directed to an electrode assembly for an electrode catheter system. The electrode assembly has a longitudinal axis, a proximal end and a distal end, and comprises at least two struts each comprised of a thermoplastic material and extending coextensively with each other from the proximal end to the distal end of the electrode assembly. Each strut includes at least one electrode, and the electrode assembly is configurable between a collapsed configuration and an expanded configuration.

In another embodiment, the present disclosure is directed to an ablation catheter system comprising a handle, an elongate shaft extending from the handle and an electrode assembly carried by the shaft and having a longitudinal axis, a proximal end and a distal end, the electrode assembly comprising at least two struts each comprised of a thermoplastic material and extending coextensively with each other from the proximal end to the distal end of the electrode assembly, wherein each strut includes at least one living hinge and least one electrode, and wherein the electrode assembly is configurable between a collapsed configuration and an expanded configuration.

In another embodiment, the present disclosure is directed to an electrode basket strut. The strut comprises a thermoplastic material and an electrode.

In another embodiment, the present disclosure is directed to a method of making an electrode basket strut. The method includes heat pressing a thermoplastic tubular material to form a partially flattened tubular material and introducing an electrode into or onto the partially flattened tubular material.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
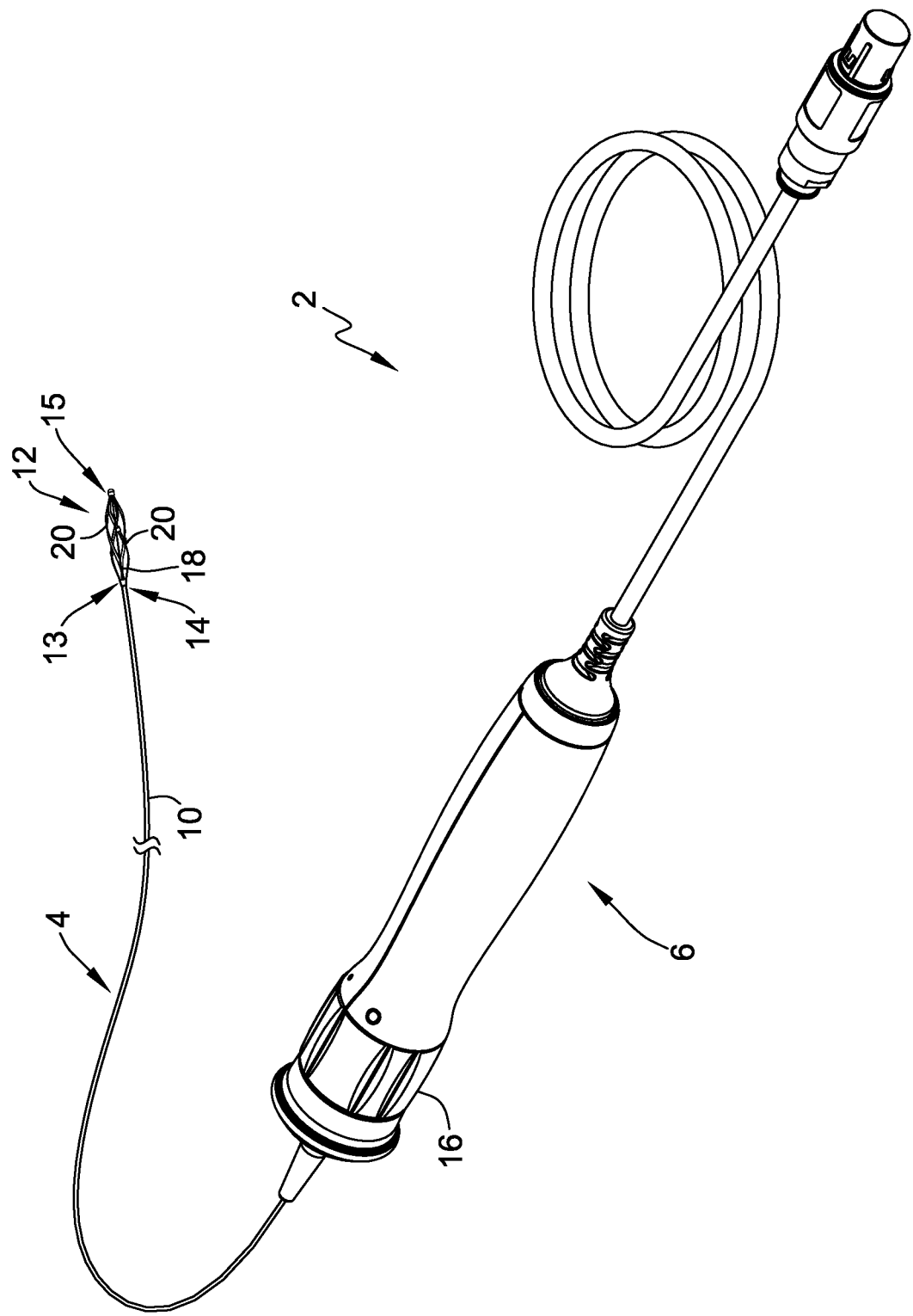
FIG. 1 is a perspective view of one embodiment of a catheter system including a handle, a catheter and an electrode assembly having multiple electrodes, with the electrode assembly being in a collapsed configuration.

The present disclosure provides ablation catheter systems and electrode assemblies and electrode baskets for use in the ablation catheter systems that include one or more struts that are manufactured from a thermoplastic material that has melt and flow characteristics. The thermoplastic based struts in accordance with the present disclosure may be utilized in electrode baskets that include any number of struts in any design formation. Common examples include electrode baskets having two, three, four, five or six or more total struts. An electrode basket may include only thermoplastic-based struts as disclosed herein, or it may include a combination of thermoplastic struts and struts based on a memory alloy, such as nitinol, or other material.

In many embodiments, the electrode assembly includes two struts that are manufactured from a single piece of heat-treated thermoplastic material. The struts are generally configured in the electrode assembly to operate in an expanded double diamond formation, although an electrode basket including the struts described herein may include two, three, four or more diamonds or other shapes in accordance with the present disclosure. The diamonds present in the formation may be of the same size, or may be of different sizes (such as for a tapered design for tapered vessels). In many embodiments, the struts in a double diamond formation are set in an expanded or collapsed configuration using an internal or central lumen within an outer catheter connected to a catheter handle. The thermoplastic struts may be constructed using traditional heat presses or irons, or may in some embodiments be produced by an injection molding and/or extrusion process.

By manufacturing the electrode basket struts from a thermoplastic material as described in the present disclosure, the struts may be manufactured with sufficient strength and rigidity without the need for a nitinol or metallic frame, thus reducing the overall cost of the strut, as well as overall manufacturing time and complexity. Additionally and significantly, the use of a thermoplastic material that has melt and flow characteristics for the strut negates the need for the use of adhesive materials in the strut and electrode basket manufacturing process, which simplifies the manufacturing process and reduces costs, while improving overall reliability and strength of the strut. Moreover, because the thermoplastic materials used to construct the struts are self-insulating, there is no need to use a polymer or thermoplastic coating that nitinol-based struts require to be electrically insulated during operation, which further reduces costs and improves efficiency. The thermoplastic-based struts as described in the present disclosure may be easy used and integrated with different types of catheter systems, including those systems that use pull wires to collapse and expand an electrode basket, and those systems that use an internal or central lumen to collapse and expand an electrode basket (e.g., over-the-wire catheter systems that include a guidewire).

In some embodiments described herein, the thermoplastic-based struts include one or more electrodes on the exterior of the struts; that is, the electrode encircles the exterior of the strut with the electrode wiring being routed through the strut to a catheter handle or other device. In other embodiments, the thermoplastic-based struts include one or more embedded electrodes; that is, the electrode is partially embedded within the strut such that only a portion of the electrode protrudes from the strut and contacts tissue during an ablation procedure, with the electrode wiring being routed through the strut to a catheter handle or other device. Combinations of external and embedded electrodes are also within the scope of the present disclosure.

Figure 2:
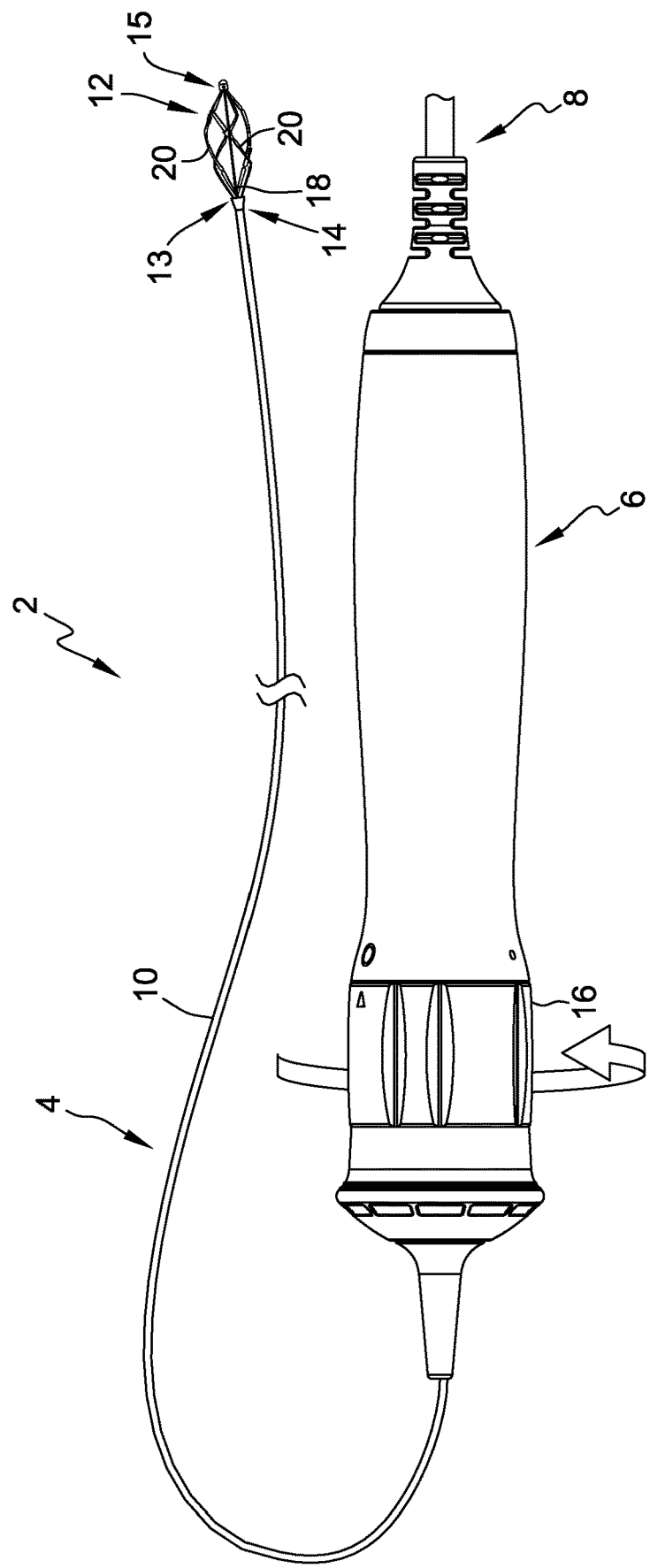
FIG. 2 is a side elevation of the catheter system of FIG. 1, with the electrode assembly being in an expanded configuration resulting from rotation of a rotatable actuator.

Referring now to the drawings, and in particular to FIGS. 1 and 2, a conventional catheter system 2 is shown by way of background and reference. Catheter system 2 includes a flexible catheter 4, a handle 6 to which flexible catheter 4 is connected, and a conductor assembly 8 for electrically connecting catheter system 2 to a suitable power supply (not shown). As one example, catheter system 2 illustrated and described herein is suitably constructed for use as an ablation system, such as a renal or heart ablation system. More particularly, illustrated catheter system 2 is a multi-electrode renal denervation system. One example of such a catheter system 2 is currently made by St. Jude Medical, Inc. under the trade name EnligHTN. General operation of a multi-electrode renal denervation system is known to those of skill in the art and is not described further herein except to the extent necessary to describe the present embodiments. It is also understood that catheter system 2 may be used for any other suitable treatment or purpose without departing from the scope of this disclosure. Additionally, while catheter system 2 is illustrated and described herein as including flexible catheter 4, catheter system 2 may further include other components used, for example, to guide flexible catheter 4 into the patient—such as, without limitation, a relatively more rigid guide catheter (not shown) or guide wire (not shown).

Flexible catheter 4 includes an elongate, flexible hollow shaft 10 connected to handle 6 at or near a proximal or rear end of the catheter shaft (not shown because it is hidden by a connector at the front end of handle 6), and an electrode assembly 12 disposed at or near a distal or front end 14 of flexible hollow shaft 10. Electrode assembly 12 includes proximal end 13 and distal end 15. It is understood, however, that electrode assembly 12 may be disposed anywhere along flexible hollow catheter shaft 10 intermediate the proximal end and the distal end 14 thereof without departing from the scope of this disclosure. As used herein, the terms proximal and front, and distal and rear, are used with reference to the orientation of catheter system 2 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to handle 6 while the terms distal and front refer to a longitudinal position that is relatively farther from handle 6.

Illustrated electrode assembly 12 is in the form of what may be referred to as an electrode basket and includes struts 20, and is suitably configurable between a collapsed configuration (FIG. 1) for maneuvering and positioning the electrode assembly in the patient, and an expanded configuration (FIG. 2) for operation of the electrode assembly to perform a desired procedure such as an ablation procedure. An annular (e.g., ring-shaped) actuator 16 is mounted on handle 6 for rotation relative thereto and is operatively connected to electrode assembly 12 for selectively configuring the electrode assembly between its collapsed and expanded configurations. It is understood that another suitable actuator (e.g., slide, push button, lever, etc.) may be used instead of rotating actuator 16 to selectively configure electrode assembly 12 without departing from the scope of this disclosure. In some embodiments, electrode assembly 12 may be selectively adjustable between an infinite number of configurations (e.g., degrees of expansion) between its collapsed and expanded configurations using actuator 16.

A control line, such as a suitable cable or pull wire 18 extends from electrode assembly 12 within hollow catheter shaft 10 and into the handle 6 for operative connection with the actuator to thereby operatively connect the actuator 16 with electrode assembly 12. In some embodiments two or more pull wires, cables or other suitable control lines or tubes may be used for selectively configuring electrode assembly 12. It is also understood that control line 18 may be any suitable control line other than a pull wire, such as a cable, string, tie, compression member or other suitable control to operatively connect electrode assembly 12 to actuator 16. A suitable electrical wire bundle (not shown) also extends through hollow catheter shaft 10 from handle 6 to electrode assembly 12 to deliver power to, and receive feedback from, electrode assembly 12.

As noted above, the present disclosure includes struts (generally arranged in an expanded double diamond configuration, although other configurations are within the scope of the present disclosure) for an electrode assembly or electrode basket that are constructed of a thermoplastic material that has melt and flow characteristics. As used herein, the term "thermoplastic material" refers to a material that becomes plastic upon heating providing flow properties and that hardens upon cooling and is able to repeat these procedures. The thermoplastic material used to construct the struts as disclosed herein is generally in the shape of a tube, although other shapes and configurations are within the scope of the present disclosure. Suitable thermoplastic materials for constructing the electrode basket struts as described herein include, for example, polystyrene, polyvinyl chloride, ethylene vinyl acetate, polyurethanes (urethane-based materials), nylon, polyether block amides (Pebax®), and the like. Other heat settable plastics or superplastics are also suitable and known to those of ordinary skill in the art. Particularly desirable thermoplastic materials include Pebax® polyether block amides.

The thermoplastic material used to construct the struts for the electrode basket has a suitable hardness and rigidity such that the resulting strut is sufficiently strong and durable when utilized in the electrode basket. In many embodiments, the thermoplastic material will have a durometer value of from 30 Shore A to 100 Shore A, including from 40 Shore A to 90 Shore A, including from 50 Shore A to 80 Shore A, including form 60 Shore A to 75 Shore A, including about 72 Shore A. Additionally, the thermoplastic material used to construct the struts for the electrode basket may have a wall thickness of from about 0.001 inches (about 0.00254 centimeters) to about 0.01 inches (about 0.0254 centimeters), including from about 0.001 inches (about 0.0025 centimeters) to about 0.008 inches (about 0.0203 centimeters), including from about 0.002 inches (about 0.0051 centimeters) to about 0.007 inches (about 0.0178 centimeters), including from about 0.003 inches (about 0.0076 centimeters) to about 0.006 inches (about 0.0152 centimeters), including about 0.005 inches (about 0.0127 centimeters). The inner diameter and outer diameter of the thermoplastic tube are not critical and may be selected based on the desired size of the strut to be constructed and the desired electrical components to be used.

Figure 3A:
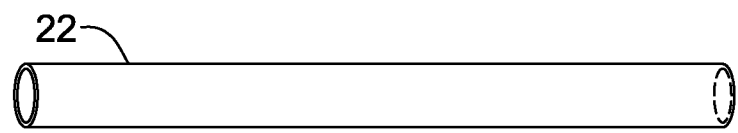
FIGS. 3A-3D illustrate various stages of a manufacturing process for struts for an electrode basket as described herein.
Figure 3B:
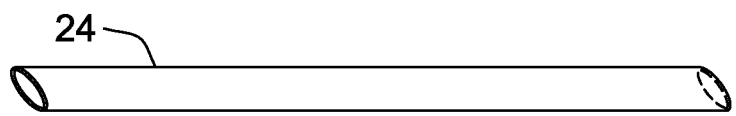

Once a suitable thermoplastic material is selected for constructing the struts, a thermoplastic tube 22 (or other thermoplastic configuration), as shown in FIG. 3A, may be heat pressed at a suitable temperature (i.e., a temperature slightly above the melting point of the thermoplastic material) to produce a thermoplastic tube 24, as shown in FIG. 3B, that has been at least partially flattened such that it is no longer circular. Other heating and pressing/flattening operations in addition to, or in place of the heat pressing, are within the scope of the present disclosure and may be suitable to flatten the thermoplastic tube. Thermoplastic tube 22 is not completely flattened and melted together to form a solid substrate, but rather is partially flattened to a desired degree to close the thermoplastic tube from about 30% to about 90%, including from about 40% to about 90%, including from about 50% to about 90%, including from about 60% to about 90%, including from about 70% to about 90%, including from about 70% to about 85%, including about 80% to about 85% such that it is not completely closed off and melted together. Thermoplastic tube 22 is not completely closed off and sealed in order to allow electrical wiring, such as electrical wiring for an electrode and/or a thermocouple (or other electric components such as sensors and the like), to be routed through flattened thermoplastic tube 24 to another part of a catheter system, including to the catheter handle.

Once thermoplastic tube 22 has been flattened to the desired degree, one or more electrodes and/or thermocouples or other electronic devices or sensors may be introduced into or onto the thermoplastic tube to be used to form the struts in an electrode basket for a catheter system as described above. In many embodiments, a single thermoplastic tube is used to construct struts (generally arranged in a double diamond configuration, although any number of diamonds or other strut configuration is within the scope of the present disclosure) for the electrode basket. Each strut may include one, two, or more electrodes, each of which may have an internal thermocouple. In many embodiments, the electrode will be a platinum electrode that includes an internal thermocouple. Of course, electrode baskets formed with more than two diamonds and more or less than four electrodes are within the scope of the present disclosure, as well as struts formed from more than one thermoplastic tube.

Figure 3C:
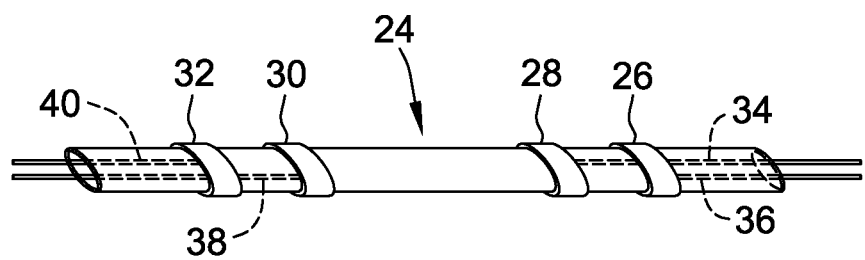

In one illustrated example, and now referring now to FIG. 3C, there is shown partially flattened thermoplastic tube 24 including exterior electrodes 26, 28, 30, and 32, each of which encircle the exterior of flattened thermoplastic tube 24. Further shown is electrode wiring 34, 36, 38, and 40 running partially through the interior of flattened thermoplastic tube 24. Electrode wiring 34, 36, 38, and 40 is connected to electrodes 26, 28, 30, and 32 respectively, via holes (not shown as they are covered by the electrodes) in flattened thermoplastic tube 24. The holes are introduced into flattened thermoplastic tube 24 through one side of the tube to allow wiring for electrodes 26, 28, 30, and 32 (and any other electronic components) using a drill or other suitable device to introduce a hole through one side of the thermoplastic material. Alternatively, the holes may be introduced into the thermoplastic tube prior to the flattening process. In many embodiments, after the electrode or electrodes are introduced onto the exterior of the flattened tube and the wiring run internally through the tube, the thermoplastic tube and electrodes will be subjected to a second heating and flattening process to flatten and seal the electrode or electrodes on the exterior of the flattened tube. The flattening and sealing process negates the need for any adhesive to secure the exterior electrode to the thermoplastic tube. In some embodiments, a small amount of plastic filler material, which may optionally be the material that comprises the thermoplastic tube, may be used to help fill and seal any openings or rough edges around the electrodes, or other electrical components. One skilled in the art will recognize based on the disclosure herein that any electrical or other wiring present could be routed in many other alternative ways without departing from the scope of the present disclosure.

Figure 3D:
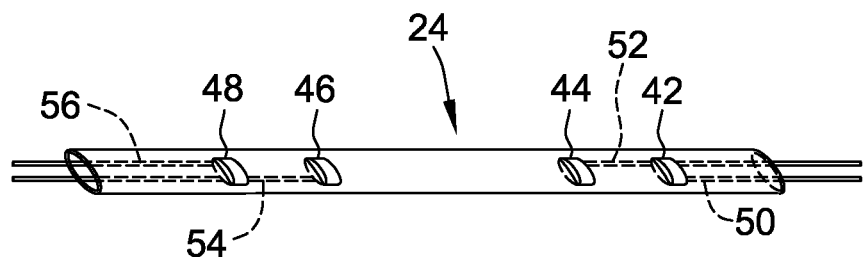

In another embodiment, after thermoplastic tube 22 has been partially flattened and one or more holes introduced into one side of the tube as noted above, one or more electrodes may be introduced into, or embedded into, the hole or holes such that the electrode or electrodes are partially contained within flattened thermoplastic tube 24 and only partially protrude from the hole in flattened thermoplastic tube 24. Referring now to FIG. 3D, there is shown flattened thermoplastic tube 24 including embedded electrodes 42, 44, 46, and 48, and embedded electrode wiring 50, 52, 54, and 56. Generally, embedded electrode wiring 50, 52, 54, and 56 will be fed through the holes in flattened thermoplastic tube 24 and then the electrodes introduced into the holes such that approximately the bottom half or bottom two thirds of each of the electrode is located within flattened thermoplastic tube 24 and the top half of the electrodes protrude out of flattened thermoplastic tube 24. Once embedded electrodes 42, 44, 46, and 48 have been introduced into the holes in flattened thermoplastic tube 24, in many embodiments it may be desirable to apply heat via a heat gun or other heating apparatus at the juncture of each hole and the embedded electrode to soften and melt a small amount of the thermoplastic material such that upon cooling, the melted material assumes the conformation of embedded electrode 42, 44, 46, and 48 for a tight, smooth fit and finish. In some embodiments, a small amount of plastic filler material, which may be the material that comprises the thermoplastic tube, may be used to help fill and seal any openings or rough edges around the embedded electrodes, or other electrical components.

When the thermoplastic strut includes one or more embedded electrodes as described above, the energy transfer from the electrode and into the tissue being ablated may be more efficient and thus reduce procedure time as energy delivered to the electrode is introduced directly into the tissue only; that is, because no portion of the electrode is contacting the blood in the vessel receiving the ablation procedure as the electrode is only contacting tissue when positioned and energized, the energy loss is significantly minimized or eliminated and efficiency is increased.

Once the thermoplastic strut including the electrodes, whether internal, external, or a combination of both, has been constructed, it may be utilized to form a portion of a double diamond-shaped strut configuration (or a triple or quadruple diamond etc.) for an electrode basket for use in the ablation system described above. The struts disclosed and described herein are suitable for use in ablation systems that use a pull wire configuration to open and close the electrode basket (in such systems where guide catheters as known in the art are used to guide the electrode basket to a target site), as well as ablations systems that include a guide wire (over the wire-type systems) and use a central lumen to open and close the electrode basket. Although further described herein in combination with embedded electrodes and over-the wire systems, all further disclosure is equally applicable to embodiments including exterior electrodes and/or pull wire systems.

Once the thermoplastic tube has been fitted with the electrodes, two fold lines may be introduced onto the thermoplastic tube (generally in the center region) to assist in folding the thermoplastic tube onto itself for making the struts using two folds. The folds may occur at any angle that allows the desired conformation of the thermoplastic tube to be obtained; that is, when the thermoplastic tube is folded onto itself as described herein using the fold lines, the exact angle of folding may be any angle suitable for properly positioning the folded sections of the thermoplastic tube for further processing including for example, 20 degrees, or even 30 degrees, or even 40 degrees, or even 50 degrees, or even 60 degrees or even 70 degrees or even 80 degrees or even 90 degrees.

Figure 4:
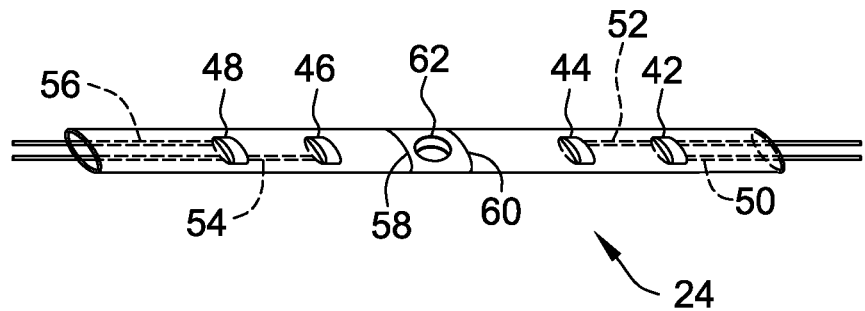
FIG. 4 illustrates a partially flattened thermoplastic tube including embedded electrodes and fold lines for preparing struts for an electrode basket as described herein.

Referring now to FIG. 4, there is shown flattened thermoplastic tube 24 including embedded electrodes 42, 44, 46, and 48 and corresponding embedded electrode wires 50, 52, 54, and 56, and further including fold lines 58 and 60. Fold lines 58 and 60 are introduced onto flattened thermoplastic tube 24 using a heated iron or other flat heated surface to score the thermoplastic material such that the thermoplastic material will easily fold upon the line in the desired area. Also shown FIG. 4 is hole 62, which is drilled through flattened thermoplastic tube 24 such that a mandrel may be inserted therethrough later in the manufacturing process as described below.

Additionally, one or more optional but desirable living hinges may be introduced onto flattened thermoplastic tube 24 to assist the formed strut in bending and flexing in a desirable manner, in a predetermined location, upon use in the electrode basket. Suitable living hinges are typically thinned or cut into a desired material (such as the flattened thermoplastic tube) to allow the rigid material on either side to bend along the line of the hinge in a predictable and repeatable desired manner. Living hinges generally have very little friction and wear and may be desirable due their ease of manufacturing as discussed below in combination with the benefits they provide.

Figure 5:
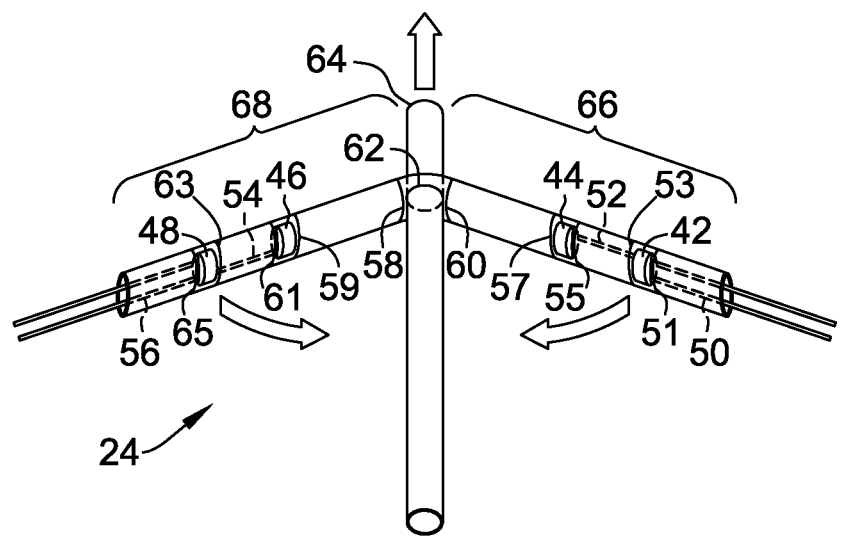
FIG. 5 illustrates the formation of thermoplastic struts from a thermoplastic tube.

When employed, living hinges will generally be introduced on both sides of the electrode to assist in the bending of the strut about the electrode. Referring now to FIG. 5, living hinges 51 and 53 are introduced onto flattened thermoplastic tube 24 on both sides of embedded electrode 42 to assist in the bending of the strut upon use. Additional living hinges 55, 57, 59, 61, 63, and 65 are also shown in FIG. 5 about their respective embedded electrodes. Similar to fold lines 58 and 60 described above, the living hinges may be introduced onto flattened thermoplastic tube 24 using a heated iron or other flat heating surface to score the thermoplastic material.

Once fold lines 58 and 60 and hole 62 have been introduced onto and into flattened thermoplastic tube 24, mandrel 64 is inserted through hole 62 and flattened thermoplastic tube 24 is folded onto itself along fold lines 58 and 60 approximately 90 degrees, as further illustrated in FIG. 5, to form a first strut 66 and a second strut 68 and generally align embedded electrodes 44 and 46 and embedded electrodes 42 and 48. Mandrels are known in the art, and a suitable mandrel 64 may be a Teflon® coated rod such that the mandrel may be removed at the end of the manufacturing process without adhering to any of the thermoplastic or other material used in the construction.

Figure 6:
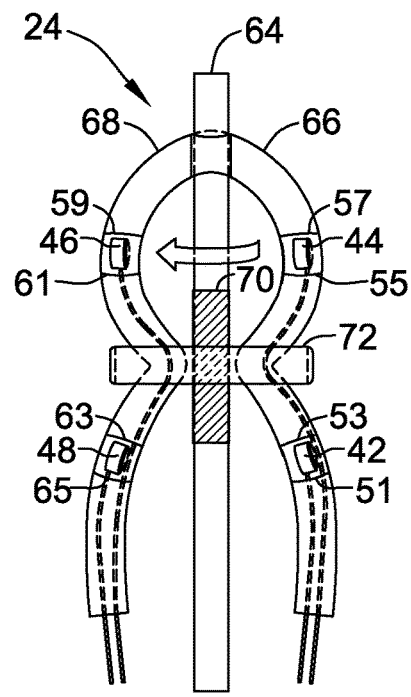
FIG. 6 illustrates the incorporation of an activation stop into an electrode basket.

Referring now to FIG. 6, after the folding along fold lines 58 and 60 is complete and first strut 66 and second strut 68 are formed, an optional activation stop 70 may be introduced over mandrel 64 and positioned about midway between embedded electrodes 44 and 46 and embedded electrodes 42 and 48. Activation stop 70 may be included to ensure that upon the opening and use of the double diamond struts as described herein (or other formations in accordance with the present disclosure), the struts cannot become positioned such that the diamonds extend too far and ultimately collapse onto themselves; that is, activation stop 70 provides an optional mechanism to prevent the accidental over-opening of the struts (i.e., the over-opening of the double diamond formation, for example) and undesirable self-collapse from which recovery may be difficult. Activation stop 70 may be constructed of any thermoplastic or similar material, and is desirably constructed of the material utilized for the thermoplastic tube. As will be recognized by one skilled in the art based on the disclosure herein, one or more other or alternative activation stops could be utilized in other positions, such as at the top and bottom of the double diamonds, to not allow for diamond self-collapse upon opening.

Referring again to FIG. 6, heat shrink material 72 is then introduced around first strut 66, second strut 68, mandrel 64 and optional activation stop 70 to begin the construction of the double diamond formation. Heat shrink material 72 will have a melting point higher than the thermoplastic material used to construct struts 66 and 68 such that upon the application of heat to heat shrink material 72, the underlying thermoplastic material will melt and flow while heat shrink material 72 remains solid to hold the materials in place. Heat shrink materials for bonding thermoplastic materials are well known in the art and suitable heat shrink materials are commercially available. After heat shrink 72 is introduced, heat is applied to cause first strut 66, second strut 68, and optional activation stop 70 to melt together and become bonded together. When the heat is discontinued, first strut 66, second strut 68 and optional activation stop 70 will be bonded together and heat shrink material 72 may be cut away with a suitable cutting member, such as a razor blade. In one optional embodiment, during the heating of heat shrink material 72 and the underlying melting together and bonding of first strut 66, second strut 68, and optional activation stop 70, the portion of first strut 66 and second strut 68 located above heat shrink material 72 may be rotated about 90 degrees (or any alternative angular amount desired) with respect to the portion of first strut 66 and second strut 68 located below heat shrink material 72 such that electrodes 44 and 46 are offset about 90 degrees from electrodes 42 and 48 after the heating is complete. This electrode offset may be desirable for ablation applications. Of course, based on the disclosure herein, one skilled in the art will recognize that the portion of the struts located below the heat shrink material could be rotated with respect to the top portion of the struts to achieve the same offset angular result.

Once heat shrink material 72 is cut away as described above, first strut 66 and second strut 68 are mated together with an outside catheter member, which may be connected to the catheter handle described above for use during an ablation procedure. The outside catheter, which may include a central lumen and guidewire as described hereinbelow, may be comprised of a braided material of sufficient strength and known in the art such that torque and stress may be applied to the outside catheter during use without the outside catheter failing. For example, the outside catheter may be comprised of a polyester block amide (Pebax®) material that is reflowed with a Teflon liner. The outside catheter will have in inner diameter and an outer diameter suitably sized and configured to accommodate a central lumen, guidewire, or other components known to those of ordinary skill in the art. For example, the outside catheter may have an outside diameter of about 0.060 inches (about 0.152 centimeters) and an internal diameter of about 0.040 inches (about 0.102 centimeters).

Figure 7:
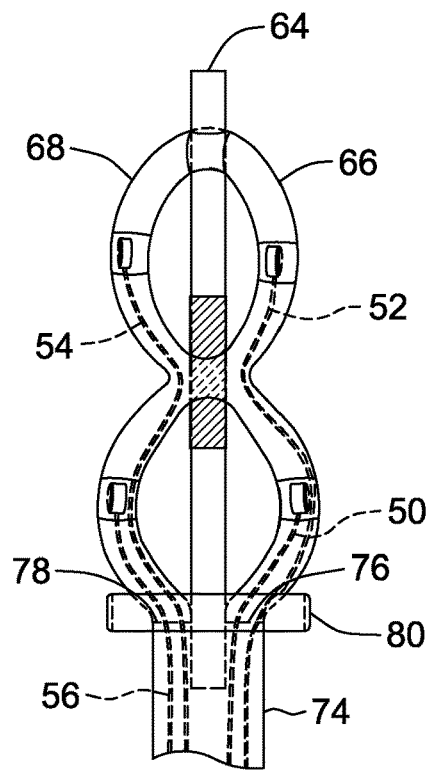
FIG. 7 illustrates the heat bonding of two thermoplastic struts to a central catheter to form a double diamond electrode basket in accordance with one embodiment of the present disclosure.

Referring now to FIG. 7, there is shown outside catheter 74, into which mandrel 64 is introduced. Electrode wires 50, 52, 54, and 56 are also routed into outside catheter 74. Once mandrel 64 is inserted into outside catheter 74, a proximal end 76 of first strut 66 and a proximal end 78 of second strut 68 are joined to outside catheter 74 using heat shrink material 80. Heat shrink material 80 will have a melting point higher than the thermoplastic material used to construct first and second struts 66 and 68 such that upon the application of heat to heat shrink material 80, the underlying thermoplastic material will melt and flow while heat shrink material 80 remains solid to hold the materials in place. Heat shrink materials for bonding thermoplastic materials are well known in the art and suitable heat shrink materials are commercially available. Heat is applied to heat shrink material 80 to cause proximal end 76 of first strut 66 and proximal end 78 of second strut 68 to melt and bond with outside catheter 74 such that first strut 66 and second strut 68 become bonded to and intimate with, outside catheter 74. Once the melting and bonding is complete, heat shrink material 80 is cut away as described above.

Figure 8:
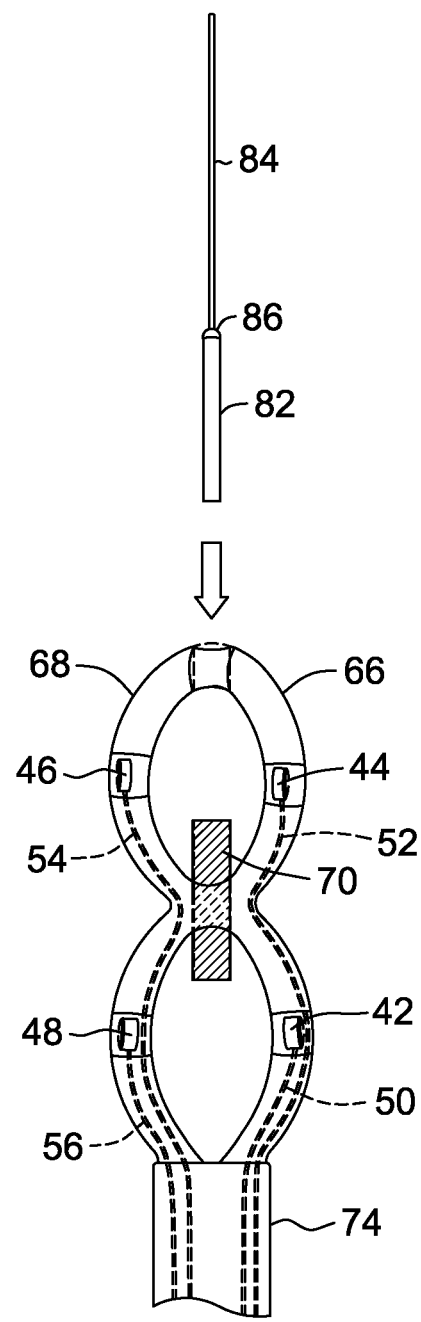
FIG. 8 illustrates the formation of an electrode basket including a center lumen and guidewire in accordance with one embodiment of the present disclosure.
Figure 9:
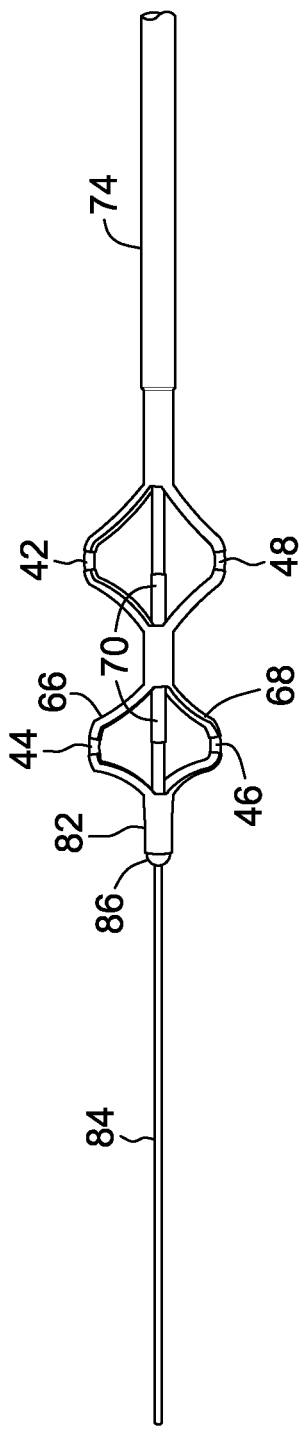
FIG. 9 illustrates a double diamond electrode basket in an expanded configuration in accordance with the present disclosure.

After first strut 66 and second strut 68 are bonded to outside catheter 74, mandrel 64 is removed from the electrode assembly and central lumen 82, which includes bead 86, and guidewire 84 are inserted in place of mandrel 64 through hole 62 and optional activation stop 70 and into outside catheter 74, as illustrated in FIG. 8. In other suitable embodiments, such as when a guide catheter system is utilized, guidewire 84 may be omitted. Wires 50, 52, 54, and 56 from electrodes 42, 44, 46, and 48 (and/or other optional electrical wires) are routed between outside catheter 74 and central lumen 82 to the handle or other component of the ablation system as described above. FIG. 9 illustrates one embodiment of an assembly formed by the manufacturing process described above.

Figure 10:
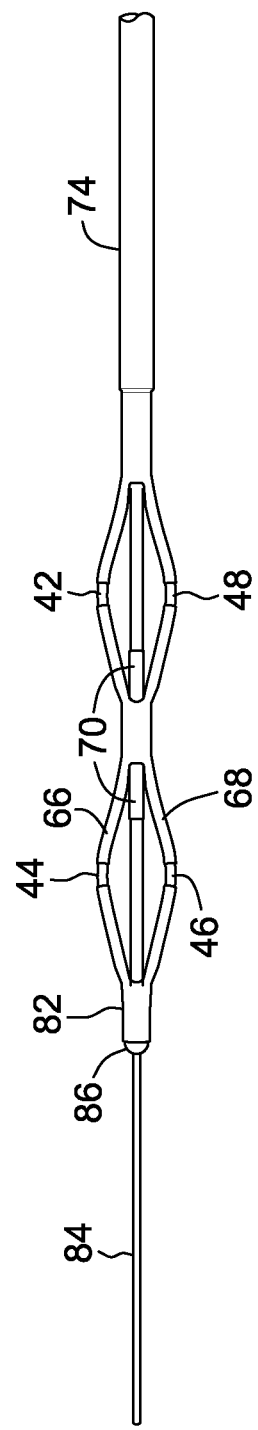
FIG. 10 illustrates a double diamond electrode basket in a collapsed configuration in accordance with the present disclosure.

Central lumen 82, shown in FIGS. 8 and 9, may be operatively connected to a handle (not shown in FIGS. 8 and 9) as described herein and utilized to configure struts 66 and 68 in an expanded or collapsed configuration during an ablation procedure. Central lumen 82 may, for example, be constructed of a braided mesh material that has sufficient column strength, torqueability, and durability to open and close the struts as described herein. In one example, the central lumen may be constructed of a braided mesh polyimide material and may have an outer diameter of about 0.0025 inches (about 0.0064 centimeters) and an inner diameter of about 0.0020 inches (about 0.0051 centimeters). Bead 86 is optionally constructed of a radiopaque material, such as platinum or other radiopaque materials known in the art, to act as a radiopaque marker during insertion of the assembly into the patient's body. Once central lumen 82, guidewire 84 and bead 86 are positioned, heat is applied about the circumference of bead 86 to melt and flow first strut 66 and second strut 68 around bead 86 and central lumen 82 to bond first strut 66 and second strut 68 to bead 86 and central lumen 82. Because central lumen 82 is bonded to first strut 66 and second strut 68, when central lumen 82 is pulled or moved toward the handle of a catheter as described herein, the struts are pulled into an expanded formation to open and form an expanded double diamond formation, as illustrated in FIG. 9. By reversing the direction of force on central lumen 82, the struts return to a collapsed configuration as shown in FIG. 10.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electrode assembly for an ablation catheter system, the electrode assembly comprising at least one strut constructed from a thermoplastic material without a metallic frame and including at least one electrode located between at least two living hinges, wherein each living hinge is formed by at least one of thinning the thermoplastic material and cutting into the thermoplastic material, wherein at least a portion of the electrode is embedded into the strut, and wherein the at least two living hinges are located about the at least one electrode such that each respective electrode is located between a respective distal living hinge and a respective proximal living hinge.

2. The electrode assembly of claim 1 wherein the thermoplastic material is a partially flattened, such that it is no longer circular, tubular thermoplastic material.

3. The electrode assembly of claim 1 wherein the thermoplastic material is an injection molded thermoplastic material.

4. The electrode assembly of claim 1 wherein the thermoplastic material is selected from the group consisting of urethane-based materials, nylon, polyether block amides, and combinations thereof.

5. The electrode assembly of claim 4 wherein the thermoplastic material has a durometer value of from 30 Shore A to 100 Shore A.

6. The electrode assembly of claim 4 wherein the thermoplastic material has a durometer value of from 60 Shore A to 75 Shore A.

7. The electrode assembly of claim 4 wherein the thermoplastic material has a durometer value of about 72 Shore A.

8. The electrode assembly of claim 1 wherein the assembly includes two struts.

9. The electrode assembly of claim 8 wherein the two struts are fabricated from a single thermoplastic tube.

10. The electrode assembly of claim 8 wherein the assembly includes at least one activation stop.

11. The electrode assembly of claim 1 wherein the assembly further includes a pull wire.

12. The electrode assembly of claim 1 wherein the electrode assembly is an over the wire electrode assembly.

13. The electrode assembly of claim 1 wherein the strut is metallic-free and the electrode assembly is adhesive-free.

14. An ablation catheter system comprising:
a handle,
an elongate shaft extending from the handle
an electrode assembly carried by the shaft and having a longitudinal axis, a proximal end and a distal end, the electrode assembly comprising at least two struts each constructed from a thermoplastic material without metallic frames and extending coextensively with each other from the proximal end to the distal end of the electrode assembly, wherein each strut includes at least two living hinges located about at least one electrode such that each respective electrode is located between a respective distal living hinge and a respective proximal living hinge, wherein each living hinge is formed by at least one of thinning the thermoplastic material and cutting into the thermoplastic material, wherein at least a portion of each of the electrodes is embedded into the struts, and wherein the electrode assembly is configurable between a collapsed configuration and an expanded configuration.

15. The ablation catheter system of claim 14 further including a guide wire.

16. An electrode basket strut for an electrode assembly, the strut constructed from a thermoplastic material without a metallic frame and including an electrode located between at least two living hinges, wherein each living hinge is formed by at least one of thinning the thermoplastic material and cutting into the thermoplastic material, wherein the at least two living hinges are located about the at least one electrode such that each respective electrode is located between a respective distal living hinge and a respective proximal living hinge, and wherein at least a portion of the electrode is embedded into the strut.

* * * * *